United States Patent
Yarovesky (10) Patent No.: US 9,084,658 B2
(45) Date of Patent: Jul. 21, 2015

(54) PREFABRICATED COMPOSITE LAYERS FOR DUPLICATION OF TOOTH STRUCTURE AND MUCOSAL TISSUE

(75) Inventor: Uriel Yarovesky, Thousand Oaks, CA (US)

(73) Assignee: Dental Illusions, Inc., Agoura Hills, CA (US)

( * ) Notice: Subject to any disclaimer, the term of this patent is extended or adjusted under 35 U.S.C. 154(b) by 217 days.

(21) Appl. No.: 12/756,701

(22) Filed: Apr. 8, 2010

(65) Prior Publication Data

US 2011/0250565 A1  Oct. 13, 2011

(51) Int. Cl.
 *A61C 13/09* (2006.01)
 *A61C 13/01* (2006.01)
 *A61C 13/06* (2006.01)

(52) U.S. Cl.
 CPC .............. *A61C 13/09* (2013.01); *A61C 13/01* (2013.01); *A61C 13/06* (2013.01)

(58) Field of Classification Search
 USPC ............................................. 264/16
 See application file for complete search history.

(56) References Cited

U.S. PATENT DOCUMENTS 4,828,117 A * 5/1989 Panzera et al. ............... 206/63.5

* cited by examiner

*Primary Examiner* — Larry Thrower
(74) *Attorney, Agent, or Firm* — Kelly & Kelley, LLP (57) ABSTRACT

The process for duplicating mucosal tissue or tooth structure for use in a prefabricated dental restoration includes first selecting a characterization strip and a base layer having a desired oral cavity color or characteristic. The selected characterization strip is then placed on the selected base layer and the two are rolled together into a composite. The composite is then formed into a portion of a prefabricated dental restoration, wherein the color and characteristics of the composite duplicate mucosal tissue or tooth structure. In this regard, the composite may be bent into a denture base or otherwise shaped into an artificial tooth for use in dentures.

24 Claims, 5 Drawing Sheets

PREFABRICATED COMPOSITE LAYERS FOR DUPLICATION OF TOOTH STRUCTURE AND MUCOSAL TISSUE

BACKGROUND OF THE INVENTION

The present invention relates to replication of oral tissue for use in dental prosthetics. More particularly, the present invention relates to prefabricated composite layers representing oral cavity tissue characteristics for use in dental prosthetics such as dentures.

Dentures are prosthetic devices implanted in the mouth to replace missing teeth. Dentures may be supported by surrounding hard and soft tissue of the oral cavity. Conventional dentures typically replace all teeth in the oral cavity and are removable. Other denture designs rely on bonding or clipping onto teeth or other dental implants, rather than being used as a full dental replacement. In general, there are four basic types of dentures, which include: (1) complete dentures; (2) immediate dentures; (3) implant retained dentures; and (4) Cu-Sil® dentures manufactured by Present Investment Corporation of Deerfield Beach, Fla.

Complete dentures are the most common form of conventional dentures. Complete dentures replace all teeth in the oral cavity and typically attach to hard and soft tissue by a bonding agent. These dentures are typically only removable by breaking the bond between the dentures and the oral cavity tissue. Complete dentures require as much surface area as possible to maximize retention and stability of the bonding agent to the hard and soft oral cavity tissue. Specifically, the top denture is retained by "suction" and relies on the hardness of the underlying hard tissue for stability. Complete dentures represent the entire build-up of the oral cavity, including teeth and gums.

Immediate dentures are temporary dentures that are made before natural teeth are extracted. The immediate denture is basically a complete or partial denture that is inserted into the oral cavity of the patient on the same day following removal of natural teeth. The prefabricated immediate denture inserts directly over the gums once the natural teeth are extracted. The bone that supported the extracted teeth is still intact and the overlying gum tissue is relatively firm. The immediate denture acts as a band-aid to protect the underlying tissue and to reduce bleeding in areas of the extracted teeth. Like complete dentures, immediate dentures typically include artificial teeth and oral cavity tissue characteristics that need to replicate natural teeth and oral cavity characteristics.

Dental implants are permanent fixtures, e.g. titanium posts that anchor to the jawbone. The titanium posts generally integrate, i.e. further attach, to the jawbone over time—typically several months after being implanted. The denture implant attaches to the post that protrudes through the gums and into the mouth. The posts may support individual porcelain replacement teeth, bridges that screw or cement to the posts, or other types of attachments. Dentures placed over the titanium posts do not need to otherwise be anchored to the jaw. This eliminates the need to cover the entire pallet with denture-material, as done with complete dentures or immediate dentures that "suction" thereto. Accordingly, implants of this sort significantly reduce the gag reflex commonly associated with standard dentures. Implants are typically effective in anchoring otherwise non-retentive dentures. The associated dental implants that attach to the titanium posts need to comprise artificial teeth and oral cavity tissue that closely represent, in coloration and detail, natural teeth and oral cavity tissue. Applying an implant having oral cavity tissue coloration dissimilar from natural oral cavity tissue is aesthetically undesirable as the implants are readily noticeable when the patient smiles.

Over dentures are another type of implant dentures that insert over existing teeth (or remnants) as a complete or partial replacement thereof. Over dentures are most frequently used with teeth that have previously received a root canal. Assuming the roots of these teeth are still suitable, the crown of the tooth may be cut off at the gum line and a removable denture may be placed over the stumps. Sometimes, the stumps are filled with cast metal, or another material, to guard against decay. Over dentures provide stability via the roots and maintain the supporting jawbone. The jawbone would otherwise resorb, thereby leaving less tissue and bone to support the denture. Additionally, the root itself serves as a vertical support for the denture and provides more stability than would otherwise be available. As with the aforementioned dentures, over dentures also need to include artificial teeth and oral cavity tissue that closely represents natural teeth and oral cavity tissue to maximize the aesthetic results of the over dentures when implanted.

Lastly, Cu-Sil® dentures are for patients who have few good remaining teeth. These dentures provide a soft, elastomeric gasket that clasps to the neck of the natural teeth. The dentures are gently cushioned against a hard denture base to seal out food and fluids. These dentures provide suction and mechanical stability via the immobility of the nature teeth. Cu-Sil® dentures can even stabilize loose teeth and, with care, can extend the lives thereof. Cu-Sil® dentures are particularly ideal for patients unable to wear full dentures. Placing the Cu-Sil® dentures around even a single healthy tooth can help retain and stabilize the dentures in the oral cavity. Cu-Sil® dentures, especially, need to aesthetically replicate the teeth and oral cavity tissue coloration and characteristics when integrated into an oral cavity as these dentures also preferably blend in with the existing oral cavity tissue.

Each of the above-described dentures requires a partial or even full rebuild of the oral cavity tissue surrounding natural or acrylic teeth integrated with the denture appliance. Artificial tooth structure or mucosal tissue used to form the dentures should naturally replicate the oral cavity to enhance the aesthetics of the dentures.

There exists, therefore, a significant need in the art for a prefabricated composite layer that replicates the oral cavity tissue color and characteristics and that can be easily integrated with a plurality of different types of dentures. Such a dental prosthetic should include multiple oral cavity tissue coloration and characteristics formed into a unitary composite layer to duplicate the oral cavity tissue coloration and characteristics in association with tooth structure and mucosal tissue. The present invention fulfills these needs and provides further related advantages.

SUMMARY OF THE INVENTION

The process for duplicating tooth structure or mucosal tissue for use in a prefabricated dental restoration includes first selecting a characterization strip and a base layer having a desired oral cavity color or characteristic. Of course, the selected characterization strip and base layer depend on whether the desired oral cavity color or characteristic comprises a tooth structure color or characteristic or a mucosal tissue color or characteristic. In one embodiment, the selected characterization strip and base layer should generally replicate the color of mucosal tissue and be capable of replicating associated characteristics such as veins, blood vessels, bony coloration or gum tissue. In another embodiment, the selected characterization strip and base layer generally replicate the color of tooth structure and should be capable of replicating the characteristics of enamel, dentin, crazing lines, stains or hyper-calcification.

Next, the selected characterization strip is placed on the selected base layer in order to form a composite. The composite is formed by rolling the characterization strip and the base layer together. The rolling step includes the step of interspersing the characterization strip within the base layer. Preferably, the characterization strip is at least partially visible in the resultant composite. The characterization strip and the base layer are also preferably formed into a solid unitary structure. This may be accomplished by compressing the characterization strip and the base layer together, lightly heating the characterization strip and the base layer together, or otherwise mechanically or chemically forming the characterization strip and the base layer into the composite.

Next, the composite is formed into a portion of a prefabricated dental restoration such that the color and characteristics of the composite duplicate mucosal tissue or tooth structure. In one embodiment, the selected characterization strip and base layer comprising the composite are bent into a denture base. In an alternative embodiment, the characterization strip and the base layer comprising the composite are shaped into an artificial tooth. The composite may be preheated into a malleable substrate in order to accomplish either the bending or the shaping steps described above. After performing the bending or the shaping steps, the composite is preferably hardened through curing the composite in an oven. The resultant composite is thereby formed into a portion of a prefabricated dental restoration wherein the color and characteristics of the composite duplicate tooth structure or mucosal tissue.

The process for duplicating tooth structure or mucosal tissue for use in a prefabricated dental restoration may further include selecting a second base layer having the desired oral cavity color or characteristic. As with the characterization strip and the base layer, the second base layer has a selected oral cavity color or characteristic representative of tooth structure or mucosal tissue structure, depending on the application. Accordingly, the composite is placed on the second base layer and rolled together to form a second composite. The second composite includes additional color and characteristics representative of the desired tooth structure or mucosal tissue. Accordingly, the characterization strip and the base layer are at least partially visible in the second composite. In one embodiment, the characterization strip, the base layer or the second base layer may comprise wax. In turn, the second composite is formed into the portion of the prefabricated dental restoration such that the color and characteristics of the second composite duplicate tooth structure or mucosal tissue.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
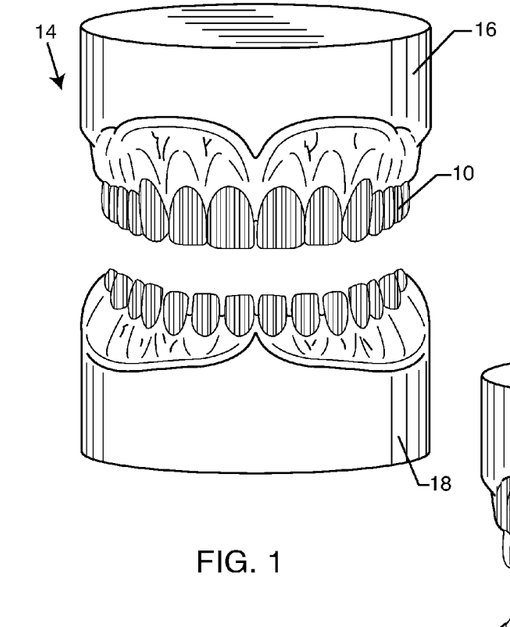
FIG. 1 is a perspective view of a set of dentures, wherein the prefabricated composite layer duplicates tooth structures.
Figure 2:
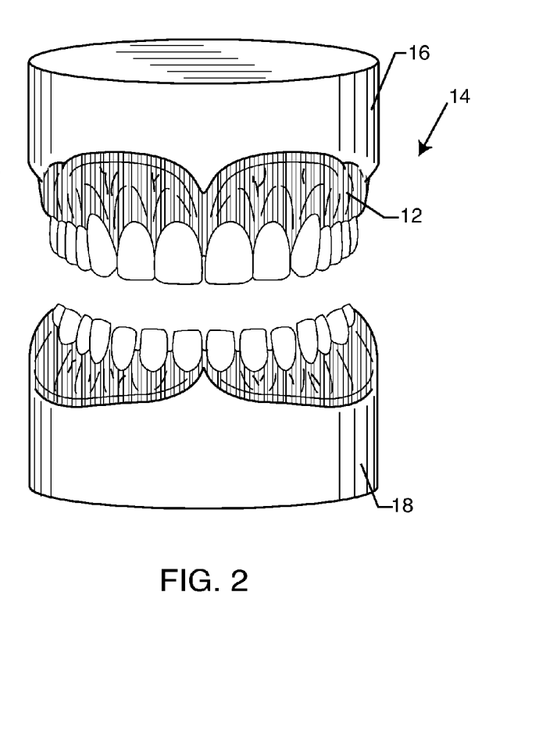
FIG. 2 is a perspective view of an alternative set of dentures, wherein the prefabricated composite layer duplicates mucosal tissue.
Figure 3:
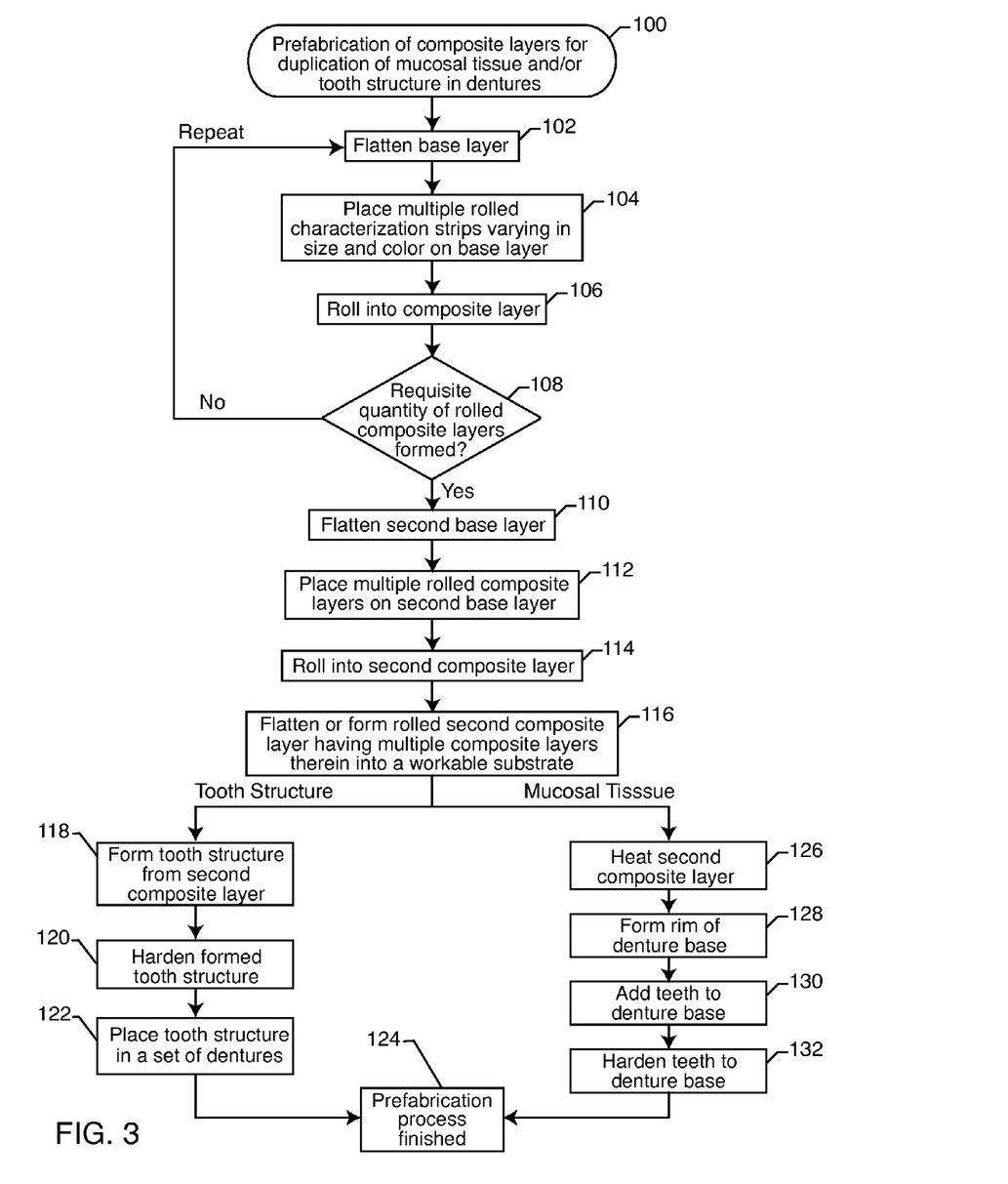
FIG. 3 is a flowchart illustrating the process for prefabricating composite layers for duplication of tooth structure and/or mucosal tissue.

As shown in the drawings for purposes of illustration, a prefabricated composite layer for the duplication of tooth structure is referred to generally by the reference number 10 in FIG. 1 and a prefabricated composite layer for duplication of mucosal tissue is generally referred to by the reference number 12 in FIG. 2. The prefabricated tooth structure 10 and the prefabricated mucosal tissue 12 include a variety of color and characteristics representative of tooth structure and mucosal tissue, respectively, as generally identified by the vertical lines in FIGS. 1-2. A preferred process associated with developing the prefabricated tooth structure 10 and the prefabricated mucosal tissue 12 is illustrated in FIG. 3. The desired color and characteristics are integrated into multiple different layers of the resultant prefabricated tooth structure 10 and the prefabricated mucosal tissue 12, as described in more detail below. These colors and characterizations are visible within the prefabricated composite and replicate lifelike oral cavity features. The prefabricated tooth structure 10 and the prefabricated mucosal tissue 12 are both preferably integrated into a set of dentures 14 as shown in FIGS. 1-2. Of course, the prefabricated tooth structure 10 and the prefabricated mucosal tissue 12 could be integrated into any one of a number of different types of dentures, including complete dentures, immediate dentures, implant retained dentures or Cu-Sil® dentures. A person of ordinary skill in the art will readily recognize that the process for prefabricating composite layers representative of oral cavity color and characteristics disclosed herein may have multiple applications outside of use with dentures, wherein replication of natural color and characterizations of tooth structure and mucosal tissue is desired. The embodiments disclosed herein with respect to prefabricating tooth structure 10 and prefabricating mucosal tissue 12 with respect to full dentures is merely a preferred embodiment.

The dentures 14 shown in FIGS. 1 and 2 generally comprise an upper portion 16 and a lower portion 18. The dentures 14 are basically formed from an impression of the oral cavity of a patient. The impression is used in conjunction with the process disclosed herein to build-up tooth structure and mucosal tissue representative of those features in the oral cavity of the patient. The upper portion 16 represents an impression taken of the upper oral cavity portion of the patient, while the lower portion 18 represents an impression taken in the lower oral cavity portion of the patient. The prefabricated tooth structure 10 and the prefabricated mucosal tissue 12, as described herein in more detail, is worked up to represent the desired color and characteristics of the oral cavity and is otherwise used to form the dentures 14 comprising the upper portion 16 and the lower portion 18.

Figure 4:
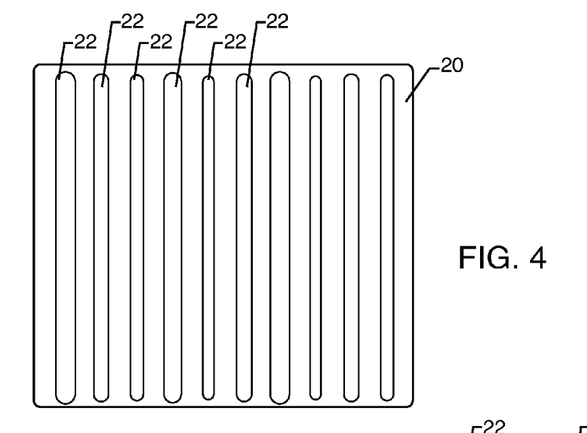
FIG. 4 is a top view of a base layer having multiple characterization strips disposed thereon.
Figure 5:
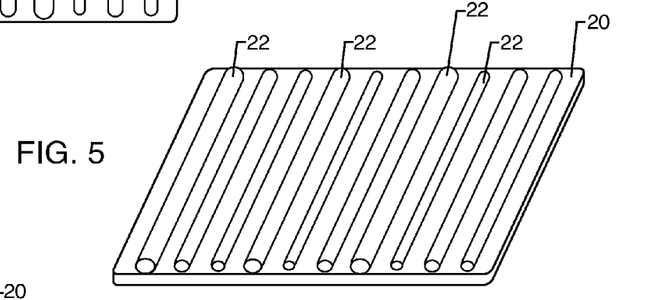
FIG. 5 is a perspective view of the base layer of FIG. 4, including the characterization strips.

FIG. 3 is a flowchart illustrating preferred steps for prefabricating composite layers for duplication of mucosal tissue and/or tooth structure in dentures (100). The first step in the prefabrication process (100) is to flatten a base layer (102), such as a base layer 20 as shown in FIG. 4. Preferably, this base layer 20 comprises a wax material that can be rolled or formed and otherwise integrated with other wax material, and later hardened into the prefabricated tooth structure 10 or the prefabricated mucosal tissue 12. After performing the flattening step (102), multiple rolled characterization strips varying in size and color are then placed on the base layer (104). A plurality of characterization strips 22 are shown in roll form applied to a surface of the base layer 20 in FIGS. 4 and 5. The characterization strips 22 may vary in length, width, thickness, coloration, etc. In a particularly preferred embodiment, the characterization strips 22 are each individually made and are not necessarily identical in size or shape. In this regard, the characterization strips 22 used with the base layer 20 and formed in accordance with the steps described below should replicate mucosal tissue and tooth structure in accordance with natural characterizations in the oral cavity of a specific patient. Such characterizations are not necessarily evenly distributed throughout the structure comprising the prefabricated tooth structure 10 or the prefabricated mucosal tissue 12 to mitigate any potential artificial appearance.

Moreover, the characterization strips 22 add coloration and characteristics to the otherwise consistently colored base layer 20. Preferably, these characterization strips 22 are at least partially viewable through the base layer 20 upon completion of the process for making the prefabricated tooth structure 10 or prefabricated mucosal tissue 12. Ideally the characterization strips 22 eventually replicate internal or external structures and coloration of teeth and oral cavity tissue, comprising teeth, enamel, dentin, crazing lines, stains, veins, blood vessels, bony coloration, hyper-calcification, mucosal tissue or gum tissue. The characterization strips 22 may also be configured to replicate other natural or unnatural effects that affect the visual appearance of the tooth or oral cavity tissue color and characteristics.

Figure 6:
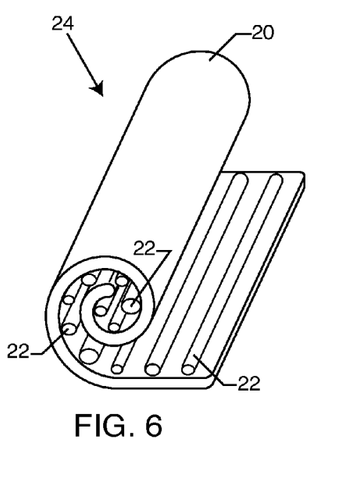
FIG. 6 is a perspective view illustrating an initial step of rolling the base layer.
Figures 7, 8:
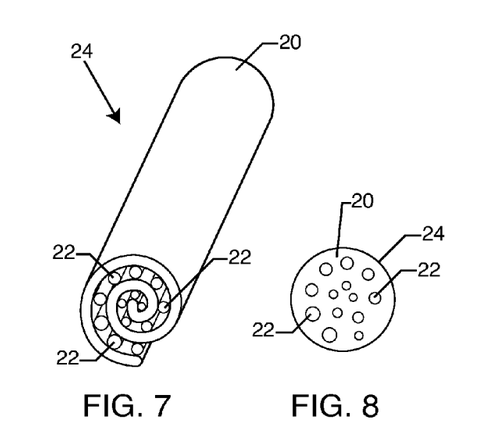
FIG. 7 is a perspective view of the base layer and the characterization strips rolled together into a composite layer.
FIG. 8 is an end view of the rolled composite layer of FIG. 7.

The next step shown in FIG. 3 is to roll the composite layer (106). FIGS. 6-8 illustrate a composite layer 24 roll formed from the base layer 20 and the characterization strips 22. As shown starting in FIG. 6, the flexible base layer 20 is simply rolled upon itself having the characterization strips 22 thereon. Preferably, the characterization strips 22 are at least somewhat attached or otherwise affixed to the surface of the base layer 20 so that the characterization strips 22 remain somewhat equally spaced during the rolling step (106). FIG. 7 illustrates the base layer 20 being continually folded upon itself such that the plurality of characterization strips 22 are held within interspersed layers therein. The composite layer 24 is thereafter compressed such that the base layer 20 and the characterization strips 22 engage and form into one another. In this regard, the resultant composite layer 24 should be a solid material that does not otherwise have any gaps or holes therein. The composite layer 24 may be lightly heated in this regard to ensure that the characterization strips 22 adequately engage and form into the structure of the base layer 20. Eliminating holes or gaps in the composite layer 24 ensures maximum structural stability of the resultant prefabricated tooth structure 10 or the prefabricated mucosal tissue 12. Compressing the base layer 20 and the characterization strips 22 together in this regard may be preferred. The characterization strips 22 preferably end up interspersed within the diameter of the resultant composite layer 24 as shown in FIG. 8. The positioning of the characterization strips 22 within the interior of the base layer 20, and further therein in accordance with the steps described below, provides multiple coloration and characteristics that vary in concentration and visibility depending on the resultant location of the characterization strips 22 in the resultant prefabricated tooth structure 10 or the prefabricated mucosal tissue 12. As shown in FIG. 3, steps (102)-(106) may be repeated until the requisite quantity of rolled composite layers are formed (108). Multiple composite layers 24 are used in association with the next step of flattening the second base layer (110).

Figure 9:
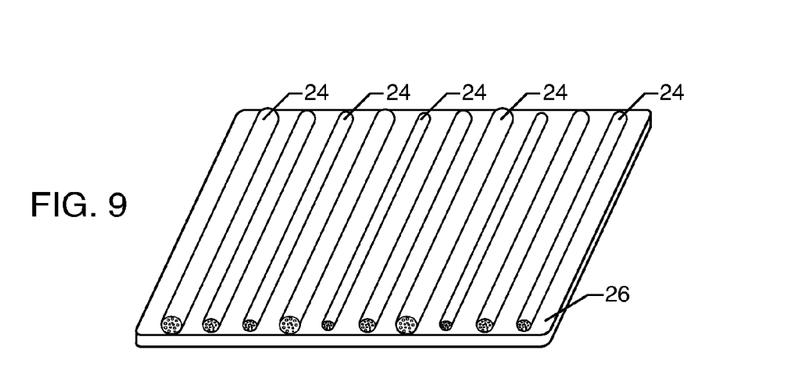
FIG. 9 is a perspective view of a second base layer having multiple rolled composite layers disposed thereon.

FIG. 9 illustrates a second base layer 26 in a substantially planar form as a result of the flattening step (110). The second base layer 26 is preferably flattened (110) into a similar size and shape as the base layer 20. To a certain extent, the size of the base layer 20, the characterization strips 22 and the second base layer 26 will be of approximate size and thickness. Of course, the size and thickness may vary somewhat depending on the size and consistency of the oral cavity to which the prefabricated tooth structure 10 or prefabricated mucosal tissue 12 is to be applied. But, as a general guideline the base layer 20 and the second base layer 26 are of comparable width and length once the dentist or lab technician determines the size of the dentures 14 for the patient. Similarly, the characterization strips 22 are of a similar length as the base layer 20 and the second base layer 26 to ensure that the desired color and characteristics extend through the entire prefabricated tooth structure 10 or the prefabricated mucosal tissue 12. Moreover, the base layer 20, the characterization strips 22 and the second base layer 26 are flexible such that a dentist or lab technician may perform the rolling steps described herein. The materials that comprise the base layer 20, the characterization strips 22 and the second base layer 26 should also be capable of being compressed together, heated into one another, or otherwise compressed together to form a highly compact and consistent structure capable of being used as a dental restoration. This is particularly important as the prefabricated tooth structure 10 and the prefabricated mucosal tissue 12 are preferably used in association with some form of dentures that are used to chew food. That means that the resultant prefabricated structures must be capable of withstanding the riggers of grinding food particles. In this regard, a wide variety of materials known in the art and compatible with dental restorations may be used in association with the embodiments described herein.

Figure 10:
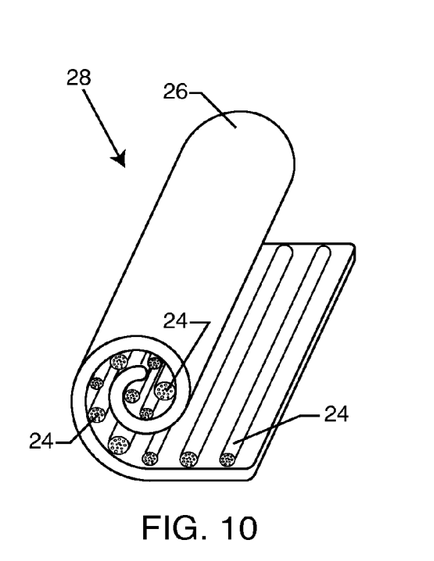
FIG. 10 is a perspective view illustrating the step of rolling the second base layer of FIG. 9.
Figure 11:
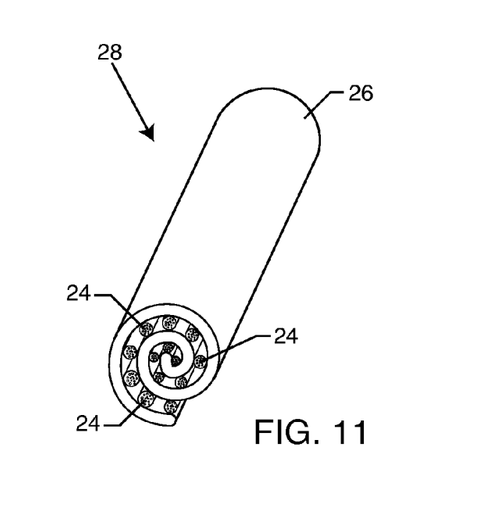
FIG. 11 is a perspective view of the second base layer and the multiple rolled composite layers rolled together into a second composite layer.
Figure 12:
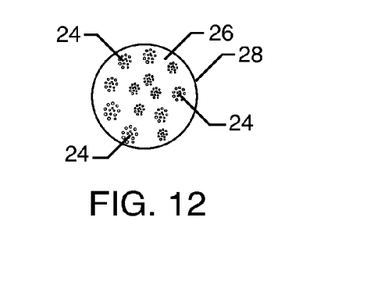
FIG. 12 is an end view of the rolled second composite layer of FIG. 11.

As shown in FIG. 3, the next step in the prefabrication process is to place multiple rolled composite layers on the second base layer (112). This process is similar to step (104), described above with respect to the base layer 20 and the characterization strips 22. Preferably, the rolled composite layers 24 at least partially attach to the surface of the second base layer 26 at the approximate intervals shown in FIG. 9. Obviously, there are numerous different types of combinations of rolled composite layers 24 that may be formed and attached to the second base layer 26 in accordance with the embodiments described herein. The rolled composite layers 24 may vary in length, width, size and consistency. Accordingly, the second base layer 26 is then rolled into a second composite layer (114). FIGS. 10 and 11 illustrate formation of a second composite layer 28 in accordance with step (114). More specifically, the rolling step (114) involves rolling the second base layer 26 upon itself such that the multiple composite layers 24 attached thereto roll into and become interspersed within the resultant second composite layer 28, similar to the step of rolling the composite layer (106). In this regard, FIGS. 10 and 11 specifically illustrate various stages of rolling the second base layer 26. Moreover, FIG. 12 is an end view illustrating the various and somewhat random positioning of the composite layers 24 disposed within the interior of the rolled second composite layer 26. As shown, the characterization strips (not enumerated in FIG. 12) are distributed as thin strips within the interior of the second composite layer 28 such that no concentration is highly visible thereof that would otherwise present unnatural looking tooth structure or mucosal tissue. Of course, the rolled composite layers 24 are formed into a consistent and unitary structure with the second base layer 26 according to the steps described above with respect to forming the composite layer 24 out of the base layer 20 and the characterization strips 22.

The next step in the process described herein is to flatten or otherwise form the rolled second composite layer having multiple composite layers therein into a workable template (116). In this regard, the second composite layer 28 must be formed according to its desired use. In one aspect, the second composite layer 28 resultant from the above-described steps could be used for either tooth structure or for mucosal tissue, depending on the application. The base layer 20, the characterization strips 22 and the second base layer 26 have selected color and characterizations to replicate either tooth structure or mucosal tissue. Obviously, any one of a number of combinations of colors may be used with the base layer 20, the characterization strips 22 or the second base layer 26 to form the desired coloration and characteristics of either tooth structure or mucosal tissue. Preferably, the prefabricated tooth structure 10 is primarily a white or off-white color having some dentin coloration, enamel coloration and other tooth characteristics and stylizations therein. On the other hand, the prefabricated mucosal tissue 12 is preferably a pinkish color and includes a variety of stylizations characteristic of gum tissue, such as veins.

Figure 13:
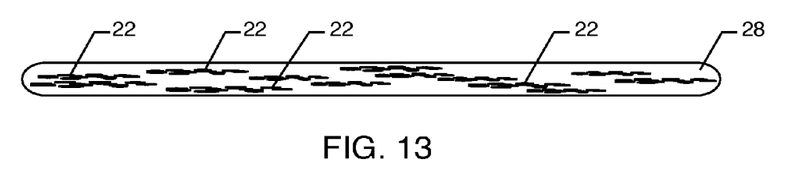
FIG. 13 is an end view of a sample prefabricated composite layer in accordance with the present disclosure.
Figure 14:
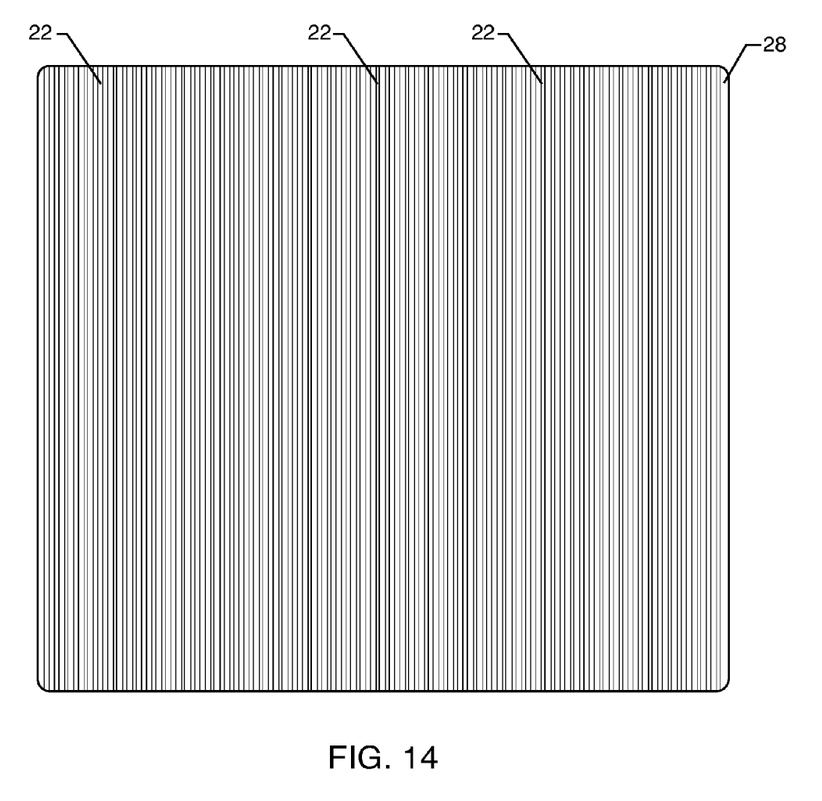
FIG. 14 is a top view of the prefabricated composite layer of FIG. 13.

When prefabricating the composite layer of tooth structure 10 (FIG. 1), the next step, as shown in FIG. 3, is to form the tooth structure from the second composite layer (118). The resultant prefabricated tooth structure 10 as shown in FIG. 1 may be formed from the composite layer 28 as shown in FIGS. 13 and 14. The prefabricated tooth structure 10 preferably replicates a tooth similar to that in size and shape of the patient receiving the dentures. In this respect, a dentist or dental technician may manipulate the second composite layer 28 in order to obtain the desired shape and size of the prefabricated tooth structure 10. Obviously, as best shown in FIG. 1, various prefabricated teeth will differ in size and shape depending on the type of tooth and the location of the tooth in the oral cavity. After the forming step (118), the model tooth is hardened by curing the formed tooth structure in an oven or kiln (120). Other processes known in the art for hardening teeth may be used in lieu of curing, such as pressing. Thereafter, the prefabricated tooth structure 10 may be placed in a set of dentures (122), as shown in FIG. 1. Subsequently, the process for creating a prefabricated composite layer of a tooth structure is finished (124).

Alternatively, the composite layer 28 may be used to form the prefabricated mucosal tissue 12 (FIG. 2). Here, the second composite layer 28 is preferably formed into a thin sheet, e.g. as shown in FIGS. 13 and 14. The next step in FIG. 3 is to lightly heat the sheet (128) such that it can be formed into the rim of the denture base (130) as shown in FIG. 2. The rim serves as the replicated gum tissue that will be used with the dentures or other dental restorations. Obviously, the coloration and characteristics of the second composite layer 28, as shown in FIG. 14, translate to the prefabricated mucosal tissue 12 as shown in FIG. 2. Of course, the dentist or dental technician will then add teeth to the replicated mucosal tissue (130) and harden the composite (132) into a wearable set of dentures. The prefabrication process for forming the mucosal tissue is then finished (124).

One important aspect of the prefabricated composite layers disclosed herein, are the placement of the characterization strips 22 within the thickness of the second composite layer 28, as generally shown in FIGS. 13 and 14. The characterization strips 22 effectively give the resultant prefabricated tooth structure 10 (FIG. 1) and the prefabricated mucosal tissue 12 (FIG. 2) the desired color and characteristics to more accurately replicate the desired oral cavity of the patient. In this regard, the resultant dentures placed into the oral cavity of the patient are more realistic.

Although several embodiments have been described in detail for purposes of illustration, various modifications may be made to each without departing from the scope and spirit of the invention. Accordingly, the invention is not to be limited, except as by the appended claims.

What is claimed is:

1. A process for duplicating mucosal tissue or tooth structure for use in a dental restoration, comprising the steps of:
   selecting a base layer having a desired oral cavity color or characteristic;
   selecting a characterization strip having a desired oral cavity color or characteristic which varies from the oral cavity color or characteristic of the base layer;
   forming the characterization strip and the base layer into a composite, wherein the characterization strip is at least partially visible in the composite; and
   forming the composite into at least a portion of a dental restoration, wherein the color and characteristics of the composite duplicate mucosal tissue or tooth structure.

2. The process of claim 1, wherein the forming the composite step comprises the step of rolling or folding the characterization strip and the base layer.

3. The process of claim 1, wherein the forming step includes the step of bending the composite into a denture base.

4. The process of claim 1, wherein the forming a dental restoration step includes the step of shaping the composite into an artificial tooth.

5. The process of claim 1, wherein the desired oral cavity color or characteristic comprises a mucosal tissue color or characteristic or a tooth structure color or characteristic.

6. The process of claim 5, wherein the mucosal tissue color or characteristic comprises veins, blood vessels, bony coloration, or gum tissue.

7. The process of claim 5, wherein the tooth structure color or characteristic comprises enamel, dentin, crazing lines, stains, or hyper-calcification.

8. The process of claim 1, further including the steps of:
   selecting a second base layer having a third desired oral cavity color or characteristic;
   forming the composite and the second base layer into a second composite, wherein the characterization strip and the base layer of the composite are at least partially visible in the second composite; and forming the second composite into at least the portion of the dental restoration, wherein the color and characteristics of the second composite duplicate mucosal tissue or tooth structure.

9. The process of claim 8, wherein the characterization strip, the base layer or the second base layer comprise wax.

10. The process of claim 1, including the steps of placing multiple characterization strips which vary in color or characteristic from one another or the base layer on the base layer and interspersing the characterization strips within the base layer.

11. The process of claim 1, including the step of heating the composite into a malleable substrate.

12. The process of claim 1, including the step of hardening the composite.

13. The process of claim 12, wherein the hardening step includes the step of curing the composite.

14. A process for duplicating mucosal tissue or tooth structure for use in a dental restoration, comprising the steps of:
   selecting a base layer having a desired oral cavity color or characteristic;
   selecting a plurality of characterization strips having desired oral cavity color or characteristic;
   interspersing the characterization strips within the base layer to add color and characteristics to the base layer and form a composite, wherein at least one characterization strip is at least partially visible in the composite;
   forming the composite into a portion of a dental restoration, wherein the color and characteristics of the composite duplicate mucosal tissue or tooth structure; and
   hardening the composite by curing the composite.

15. The process of claim 14, wherein the desired oral cavity color or characteristic comprises a mucosal tissue color or characteristic or a tooth structure color or characteristic, wherein the mucosal tissue color or characteristic comprises veins, blood vessels, bony coloration, or gum tissue and the tooth structure color or characteristic comprises enamel, dentin, crazing lines, stains, or hyper-calcification.

16. The process of claim 14, including the step of compressing the characterization strips and the base layer and bending the composite into a denture base or shaping the composite into an artificial tooth.

17. The process of claim 14, further including the steps of:
   selecting a second base layer having desired oral cavity color or characteristic;
   rolling the at least one composite and the second base layer into a second composite, wherein at least one of the characterization strips and the base layer is at least partially visible in the second composite; and
   forming the second composite into at least the portion of the dental restoration, wherein the color and characteristics of the second composite duplicate mucosal tissue or tooth structure.

18. A process for duplicating mucosal tissue or tooth structure for use in a dental restoration, comprising the steps of:
   selecting a characterization strip and a base layer having a desired oral cavity color or characteristic;
   forming the characterization strip and the base layer into a composite, wherein the characterization strip is at least partially visible in the composite and adds color or characteristics to the base layer;
   selecting a second base layer having the desired oral cavity color or characteristic;
   placing the composite on the second base layer;
   forming the composite and the second base layer into a second composite, wherein the characterization strip and the base layer are at least partially visible in the second composite;
   forming the second composite into at least a portion of a dental restoration, wherein the color and characteristics of the second composite duplicate mucosal tissue or tooth structure; and
   hardening the second composite.

19. The process of claim 18, including the steps of:
   interspersing a plurality of characterization strips within the base layer to form the composite; and
   forming the second composite into a denture base or an artificial tooth;
   wherein the desired oral cavity color or characteristic comprises a mucosal tissue color or characteristic, including veins, blood vessels, bony coloration, or gum tissue, or a tooth structure color or characteristic, including enamel, dentin, crazing lines, stains, or hyper-calcification.

20. The process of claim 2, including the step of compressing the rolled characterization strip and the base layer.

21. The process of claim 8, wherein multiple composites are interspersed in the second base layer to form the second composite.

22. The process of claim 17, wherein multiple composites are interspersed in the second base layer to form the second composite.

23. The process of claim 17, wherein the second composite forms desired coloration and characteristics of mucosal tissue, including mucosal tissue or gum tissue color, and veins, blood vessels, or bony coloration or characteristics.

24. The process of claim 17, wherein the second composite forms desired coloration and characteristics of tooth structure including enamel coloration, dentin coloration, and crazing lines, stains, or hyper-calcification characteristics.

* * * * *